United States Patent [19]

Frati et al.

[11] Patent Number: 5,769,070
[45] Date of Patent: Jun. 23, 1998

[54] DEVICE FOR THE TREATMENT OF ASTHMATIC PATIENTS, SUITABLE FOR MEASURING THE PEAK EXPIRATORY FLOW RATE AND FOR DELIVERING DRUGS USED IN THE TREATMENT OF ASTHMA

[75] Inventors: Franco Frati, Cortona; Claudio Albiani, Foiano Della Chiana, both of Italy

[73] Assignee: Istoria Farmaceutici S.p.A., Padua, Italy

[21] Appl. No.: 730,290

[22] Filed: Oct. 11, 1996

[30] Foreign Application Priority Data

Oct. 12, 1995 [IT] Italy .................................. MI95A2078

[51] Int. Cl.⁶ ............................ A61M 11/00; A62B 7/00; A62B 9/04
[52] U.S. Cl. ............................... 128/200.23; 128/202.27; 128/205.23; 128/725; 128/727
[58] Field of Search ..................... 128/200.14, 200.23, 128/203.15, 205.23, 725–727, 203.12, 202.27

[56] References Cited

U.S. PATENT DOCUMENTS

| 3,490,452 | 1/1970 | Greenfield | 128/200.23 |
|---|---|---|---|
| 3,870,046 | 3/1975 | Elliott | 128/203.15 |
| 3,921,637 | 11/1975 | Bennie et al. | 128/203.15 |
| 4,638,812 | 1/1987 | Häkkinen | 128/725 |
| 4,940,051 | 7/1990 | Lankinen | 128/200.18 |
| 5,284,133 | 2/1994 | Burns et al. | 128/203.15 |
| 5,339,825 | 8/1994 | McNaughton et al. | 128/725 |
| 5,363,842 | 11/1994 | Mishelevich et al. | 128/200.23 |
| 5,372,128 | 12/1994 | Haber et al. | 128/203.15 |
| 5,392,768 | 2/1995 | Johansson et al. | 128/200.23 |
| 5,431,154 | 7/1995 | Seigel et al. | 128/727 |
| 5,564,414 | 10/1996 | Walker et al. | 128/205.23 |
| 5,565,630 | 10/1996 | Shene | 128/727 |

Primary Examiner—Kimberly L. Asher
Attorney, Agent, or Firm—Finnegan, Henderson, Farabow, Garrett, & Dunner, L.L.P.

[57] ABSTRACT

A device is disclosed for the treatment of asthmatic patients suitable for performing the double function of peak expiratory flow rate (PEFR) meter and device for delivering drugs used in the treatment of asthma. The PEFR meter and the devices for delivering the drug are disposed in the same container, which comprises a sole rotating mouthpiece which allows the patient to select each time the function (measurement of PEFR or delivery of the drug) he means to use.

13 Claims, 4 Drawing Sheets

DEVICE FOR THE TREATMENT OF ASTHMATIC PATIENTS, SUITABLE FOR MEASURING THE PEAK EXPIRATORY FLOW RATE AND FOR DELIVERING DRUGS USED IN THE TREATMENT OF ASTHMA

FIELD OF THE INVENTION

The present invention relates to a device for the treatment of asthmatic patients, suitable for performing the double function of measuring the peak expiratory flow rate (hereinafter referred to as "PEFR") and of delivering a drug for the treatment of asthma.

PRIOR ART

The asthmatic syndromes of any type (intrinsic and extrinsic, etc.) are a very important socio-sanitary problem. The progressive increase in the air pollution and the constant increase in the number of subjects with allergic reactions reasonably lead one to believe that the number of asthmatic patients and/or the severity of the asthmatic manifestations will increase, possibly by a considerable amount. New and more efficient drugs for the treatment of the asthmatic manifestations and new diagnostic methods for determining the presence and severity of asthma are available, and enable the physician to prescribe the best treatment to each patient by deciding the treatment and the dosage appropriate for each occurrence. However, little has been done to obviate what many researchers consider the main problem in the treatment of asthmatic patients, that is, the risk that the patient will use the drug in an incongruous manner, by taking it in excessive doses or, in case of no real need, by not respecting the dosage prescribed by the physician.

Such behavior exposes the patient to the danger of drug poisoning (often caused or worsened by the synergic action of two or more drugs taken without previous medical prescription or medical control) which can be dangerous for the health of the patient and even fatal.

Some researchers and clinicians think that the risks relative to the treatment of asthmatic patients are due to an incongruous use of drugs ("beta 2 agonists", particularly) which, not having anti-inflammatory action but bronchodilatation action only, are unable to interact with pulmonary inflammation (an important morphologic condition relative to asthma), exposing the patient to severe consequences.

In the medical literature, many studies are available which prove how a careful monitoring of the parameters of lung function can improve quality of life of asthmatic patients, principally by allowing a more rational use of the different drugs in question.

Asthmatic patients have not had generally the opportunity nor the possibility to recur to sanitary personnel or to sanitary structures for such monitoring, particularly in case of exacerbations. Monitoring performed by the patient at home by means of easy-to-use meters, such as a peak flow meter, would allow the patient himself to take the drugs in question only in case of real need, and according to the dosage prescribed by the physician in relation to the severity of asthma. Such monitoring significantly helps the "self-management" of asthma by the patient himself, which is considered to be of great importance by most of those skilled in the art.

Attempts made in the past to monitor asthma at home by measurement of PEFR, at first showed encouraging results, but as the compliance of the patient progressively decreased the results deteriorated, preventing the adoption of such method at a large scale.

It is believed that the scant compliance of the patients is due to the fact that the patient, being always obliged to carry with himself at least one package of drug and the respective device for delivering the drug, considers the peak flow meter cumbersome, does not use it in case of need, and eventually stops carrying it. This reduces the quality of the management of asthma.

The subject-matter of the present invention allows one to obviate the problem, helping the patient in the management of asthma by containing in a single non-cumbersome container for performing a double function of a peak flow meter and of a device for delivering the drug used in the treatment of asthma.

Because both of these functions are always at the patient's disposal, and because the patient can easily select one function or the other one is advantageous as it allows the patient a better management of asthma. In fact, a timely measurement of PEFR succeeds in calming an anxious patient, and if the measured PEFR is normal, prevents the intake of drug in case of no real need. In case of asthma attack, the measurement itself can give the patient information relative to the dosage of drug to be taken to control the attack.

The physician, in fact, can determine for each patient PEFR values determined to be normal for the patient, and PEFR values which suggest the intake of one or more doses of drug. Such "personalized" information can be written on stick-on labels to be applied onto the external surface of the device of the present invention so that they are always at the patient's disposal.

Moreover, the present invention allows the physician and/or the patient to discriminate easily if symptoms the patient complains of (e.g. a chronic cough), not usually attributable to asthma, are related to asthma or if such symptoms must be attributed to a different pathology.

To perform this "screening" it is sufficient that the patient measures his PEFR. If the value belongs to the normal range, symptoms the patient complains of can be attributed to a pathology different from asthma and can be treated with appropriate drugs. If the PEFR value is not in the normal range, the patient will take a dose of anti-asthma drug and will repeat the measurement of his PEFR. If the new value is in the normal range (or it has neared such range), the symptoms the patient complains of can be attributed to asthma and treated accordingly, otherwise, if the new value has changed little, the symptoms can be attributed to a pathology different from asthma, and can be treated with specific drugs. Therefore, a better management of asthma by the patient is obtained by using a device according to the present invention, a not-very-cumbersome and easy-to-use device, suitable for performing the double function of peak flow meter and of device for the delivery of drugs used in the treatment of asthma.

SUMMARY OF THE INVENTION

The present invention relates to a device for the treatment of asthmatic patients and which serves the double function of measuring the peak expiratory flow rate (PEFR) and of delivering drugs used in the treatment of asthma.

Such device comprises a peak flow meter and devices for the delivery of a drug used in the treatment of asthma, disposed in the same container.

BRIEF DESCRIPTION OF THE DRAWINGS

The present invention will be clarified with reference to non limiting examples of embodiment shown in the attached drawings, wherein.

In the drawings, corresponding elements will be identified by the same numeric references.

DETAILED DESCRIPTION OF THE PREFERRED EMBODIMENT

Figure 1:
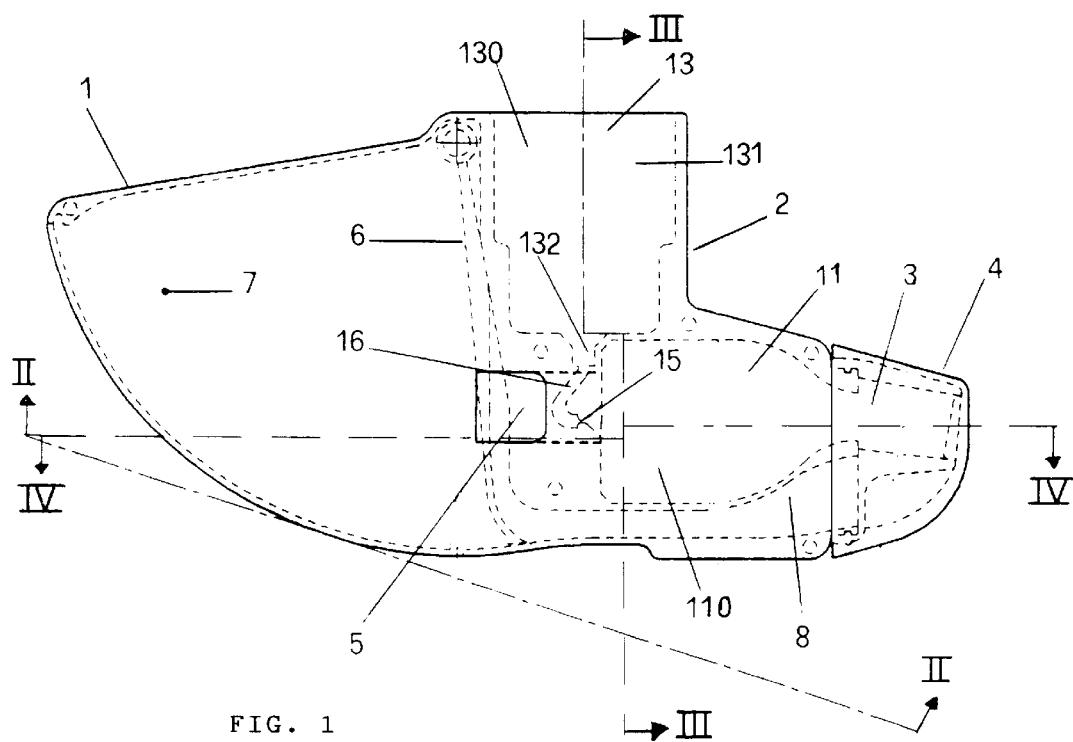
FIG. 1 is a side-view of the present invention, the internal structure of which is shown by dashed lines.
Figure 5:
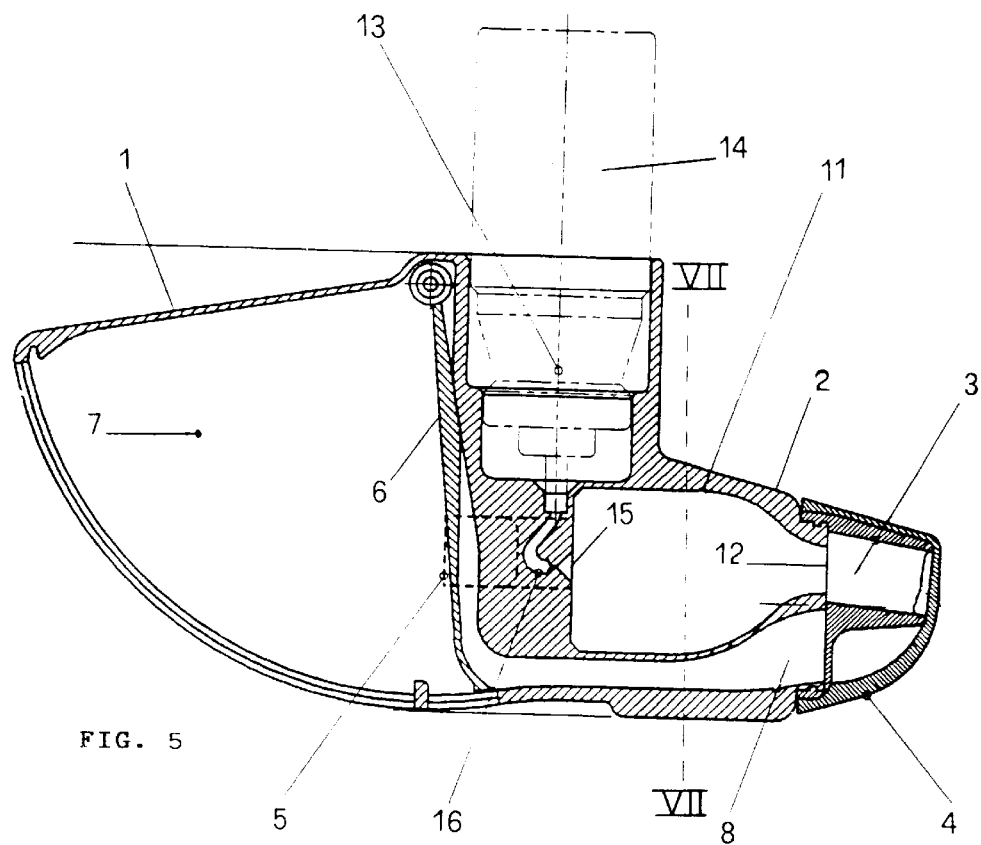
FIG. 5 is a vertical cross section of the present invention, on line V—V of FIG. 4.

FIG. 1 is a side-view of the present invention, the internal structure of which, shown in dashed lines, is more clearly shown in the vertical section of FIG. 5.

FIG. 1 shows a peak flow meter 1, a delivery device 2 suitable for delivering the drug in the form of pressurized atomized liquid, a mouthpiece 3, a protective cap 4 to cover the mouthpiece and a plurality of openings 5 (only one of which is shown in FIG. 5) provided on the side walls of the present invention to allow the air to enter the delivery device 2 and be inhaled together with the drug.

Figure 2:
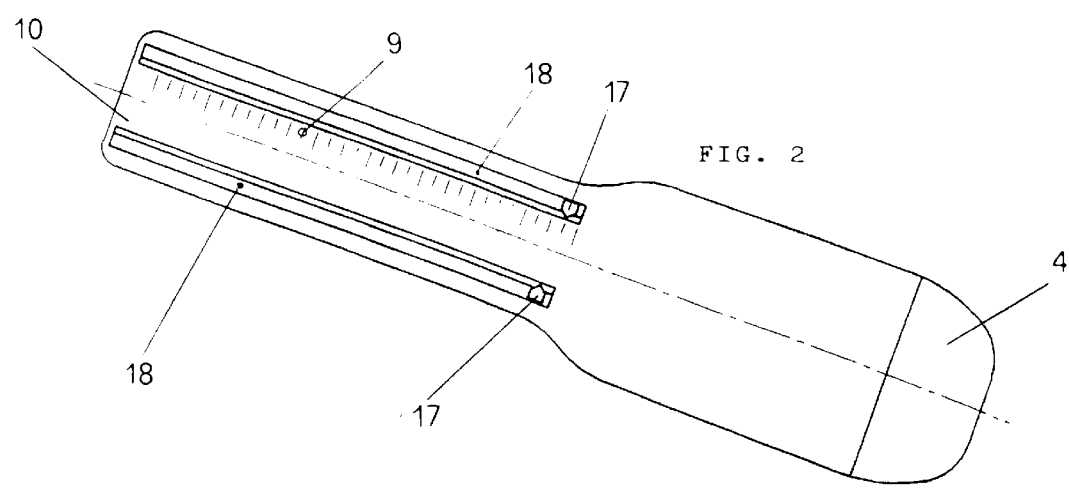
FIG. 2 is a bottom-view of the present invention, as seen on line II—II of FIG. 1.

The meter 1 shown in FIGS. 1 and 5 comprises a fin 6, hinged at one end and movable inside a cavity 7 (which has the form of a sector of circle) connected to the mouthpiece 3 by an inlet duct. The air flow expired by the patient rotates the fin 6 against the opposing force of elastic means (not shown in the figure) and the greatest rotation range of the fin 6 is read on a suitable scale 9 (FIG. 2) provided on the external face of the curvilinear wall 10 delimiting the cavity 7, thus giving a measure of the PEFR.

Without going beyond the scope of the present invention, it is possible to substitute the meter 1 shown in the figures with another known PEFR meter.

The delivery device 2 comprises a seat 13, suitable for containing the pressure cylinder 14 containing the drug (FIG. 5), connected by a duct 16 to a nozzle 15 from which the drug comes out. The nozzle 15 and the duct 16 are of known design, and the delivery device differs from the traditional delivery devices in that it comprises an expansion chamber 11, disposed between the nozzle 15 and the mouthpiece 3, for receiving the air to be mixed with the drug through openings 5 provided on the side wall of the present invention. By putting the expansion chamber 11 inside the device of the present invention, it has been possible to obtain a conveniently sized device able to mix the drug with the air better than is possible by traditional delivery devices. This results in particles of the drug being smaller and dispersed more uniformly, and reduces the speed with which the air-drug mixture gets to the patient, providing the patient with better management of the drug during inspiration and consequently allowing an optimum penetration of the active molecules into the lower airways.

In the illustrated embodiment, the expansion chamber 11 comprises a zone 110 having the shape of a cylinder sectioned by a plane parallel to its longitudinal axis (FIG. 3), connected to the outer end 12 having a shape and dimensions substantially corresponding to those of the mouthpiece 3. Experimental verifications performed by the applicant enabled compact and efficient expansion chambers 11 having the following dimensions:

cylinder diameter (zone 110): 25–30 mm (preferably 28 mm);

maximum height of zone 110: 20–25 mm (preferably 23 mm);

length of the zone 110: 17–23 mm (preferably 20 mm);

total length of the expansion chamber 11 (from the bottom of the zone 110 to the outer end 12): 30–40 mm (preferably 36 mm).

The present invention is also characterized in that it comprises a single mouthpiece 3, which the patient can rotate to select which of the measuring or drug delivery functions he wants to use by connecting the mouthpiece 3 with the outlet 12 of the expansion chamber 11 (FIGS. 1, Li, 5, 10 and 11), or connecting the mouthpiece with the inlet duct 8 of the meter 1 (FIG. 7).

Many drugs used in the treatment of asthma and of other syndromes of body air passages cough, etc.) are currently on the market and packaged in pressure cylinders MDI (Metered Dose inhaler), one of which is schematically shown and designated by numeral 16 in FIGS. 5 and 10.

Such cylinders have a cylindrical base comprising the delivery valve of the drug, a cylindrical body and a surface connecting the base to an edge of the cylindrical body. In most MDI cylinders the base and the delivery valve have the same dimensions, while the dimensions (diameter and length) of the cylindrical body and the height of the connecting surface between the base and the edge of the cylindrical body are generally so different that each cylinder is sold together with a specific delivery device, which is not generally suitable for use with different cylinders containing another drug or packaged by a different firm.

The present invention is also characterized in that the delivery device 2 has a seat 13 having shape and dimensions suitable for containing at least the majority of the pressure cylinders 14 currently on the market, allowing the patient to use the same delivery device 2 to take different drugs or drugs manufactured by different firms.

To achieve such purpose, the seat 13 has a first zone 130 having a diameter not lower than the maximal diameter of the cylindrical body of cylinders 14 currently on the market and a second zone 131 underneath the first zone 130 having a diameter not lower than the diameter of the base of cylinders 14 and a height not greater than the minimal height of the connecting surface of cylinders 14 currently on the market. The delivery valve of cylinder 14 disposed in the seat 13 is disposed in a flared hole 132 provided on the bottom of the second zone 131 and connected to the nozzle 15 by the duct 16.

FIG. 2 shows a bottom-view of the present invention, as seen on line II—II of FIG. 1. In the figure it is possible to see the external face of the curvilinear wall 10 (delimiting the cavity 7 of the meter 1) on which the graduated scale 9 is provided. Also visible are the indexes 17 which are integral with the movable fin 6 and move along the graduated scale 9 jutting out of the longitudinal slots 18 in the curvilinear wall 10, the lower wall of the duct 8, and the external side of the protective cap 4.

Figure 3:
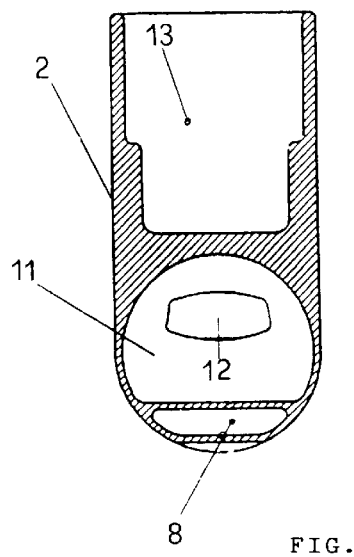
FIG. 3 is a vertical cross section of the present invention, on line III—III of FIG. 1.

FIG. 3 shows a vertical section of the present invention, cut along section line III—III of FIG. 1. In the figure it's possible to see the seat 13 and the expansion chamber 11 provided in the main body of the delivery device 2, the outlet 12 of the expansion chamber 11, and the inlet duct 8 of the meter 1.

Figure 4:
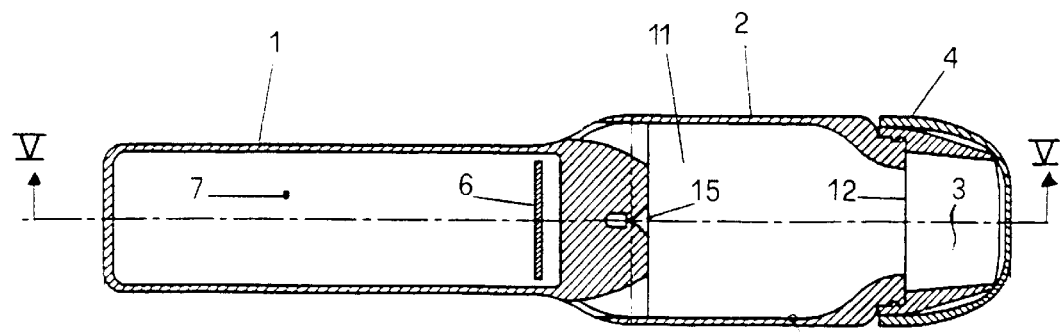
FIG. 4 is a horizontal cross section of the present invention, on line IV—IV of FIG. 1.

FIG. 4 shows a horizontal section of the present invention, cut along section line IV—IV of FIG. 1. In the figure it is possible to see the fin 6 and the cavity 7 of the meter 1, the nozzle 15 and the expansion chamber 11 comprising the outlet 12 of the delivery device, and the mouthpiece 3 covered by the protective cap 4.

FIG. 5 shows a vertical section of the present invention, on section line V—V of FIG. 4. In this figure it is possible to see more clearly the elements of the meter 1 and of the delivery device 2, including one of the openings 5, shown by a broken line, and the cylinder 14 containing the drug, placed in the seat 13.

Figure 6:
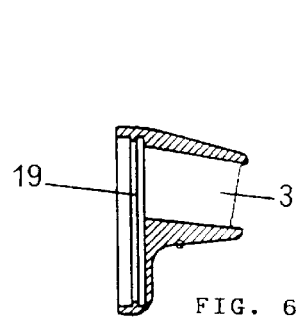
FIG. 6 shows the mouthpiece 3 of FIG. 5, separated from the rest of the device.

FIG. 6 shows the mouthpiece 3 of FIG. 5, separated from the rest of the device to point out the annular ridge 19 extending from the internal surface of the portion of the mouthpiece 3 adjacent to the main body of the delivery device which connects the mouthpiece 3 to the main body of the annular ridge of the present invention. The annular ridge connects mouthpiece 3 to the main body of the present invention by engaging a corresponding annular seat located on the external surface of said end of the main body of the present invention, thus allowing the patient to rotate the mouthpiece 3 to select the function he intends to use.

Figure 7:
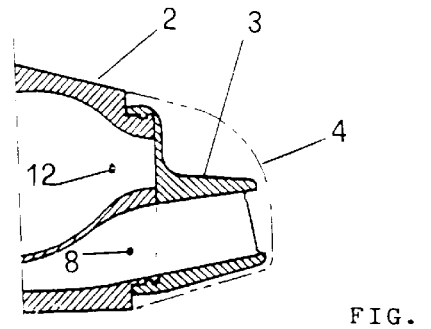
FIG. 7 shows the part of the present invention which lays at the right side of section line VII—VII of FIG. 5, wherein the mouthpiece 3 is rotated by 180° with reference to the position of FIG. 5.

FIG. 7 shows the portion of the main body of the present invention which lays at the right side of Section line VII—VII of FIG. 5, wherein the mouthpiece 3 (rotated of 180° with reference to the position shown in FIG. 5) is placed in connection with the inlet duct 8 of the meter 1.

Figure 8:
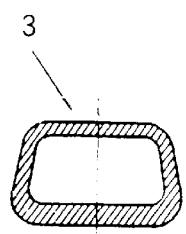
FIG. 8 is a cross section of the mouthpiece 3 of FIG. 7.

FIG. 8 shows a cross-section of the mouthpiece 3 of FIG. 7.

Figure 9:
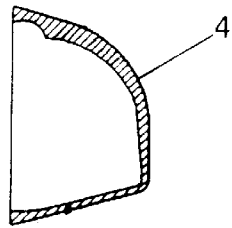
FIG. 9 is a cross section of the protective cap 4 indicated in FIG. 7 by a broken line.

FIG. 9 shows a cross-section of the protective cap 4, shown in FIG. 7 by a broken line.

Figure 10:
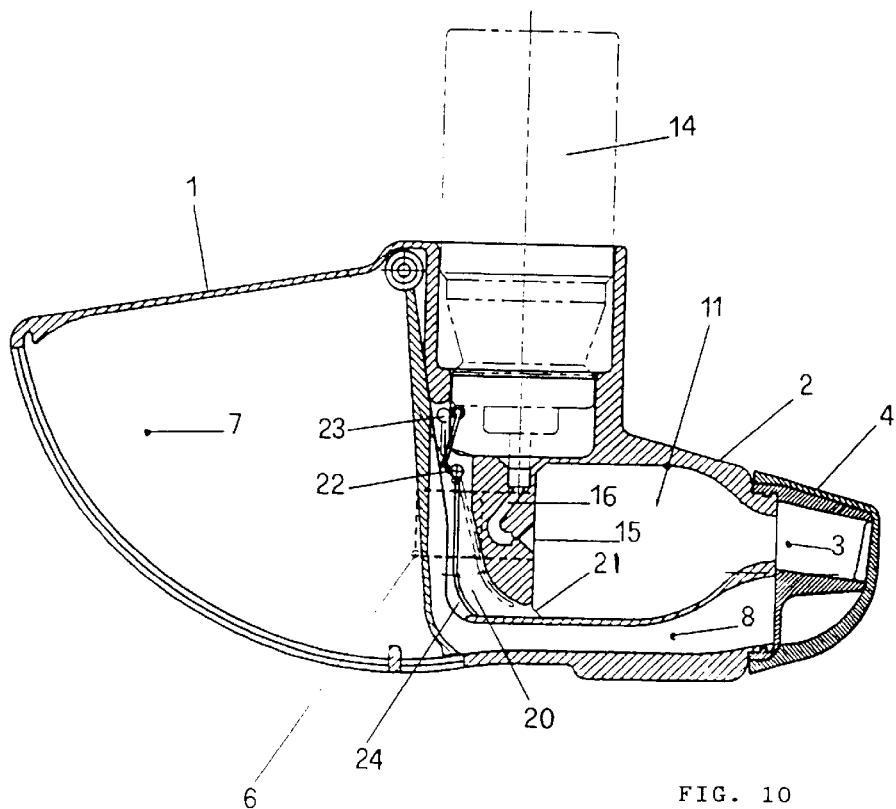
FIG. 10 is a vertical cross section, on line V—V of FIG. 4, of an embodiment of the device of FIG. 1 comprising a device started by the breath of the patient.

FIG. 10 is a vertical section, on section line V—V of FIG. 4, of another embodiment of the present device wherein the delivery device 2 comprises a device for stopping the delivery of the drug from the cylinder 14 and preventing its starting accidentally or before the patient is ready to take the drug, by only permitting the deli very of the drug when the patient inspires.

Such device includes a lever movable in a chamber 20 provided behind the part comprising the duct 16 and the nozzle 15, and connected to the expansion chamber 11 by a passage 21, such lever being pivoted on a pivot 22 disposed in the chamber 20 and being kept in a locking position (indicated in FIG. 10 by a continuous line) by elastic means not shown.

In the locking position, the thickened end of the arm 23 of the lever engages the base of the cylinder 14, blocking its downward motion and therefore preventing the delivery valve of the cylinder from being started accidentally or at the wrong moment. In response to the vacuum caused in the expansion chamber 11 by the patient when he starts to inspire to take the drug, the end of the arm 24 of the lever moves towards the expansion chamber 11, moving the lever to the position indicated in FIG. 10 by a broken line. The rotation of the lever on the pivot 22 disengages the arm 23 from the base of the cylinder 14, releasing the cylinder and allowing the patient to open the delivery valve to take the drug. To simplify the drawings, FIG. 10 does not show a pin (or similar device) which could be inserted from outside to keep the lever in the locking position.

Figure 11:
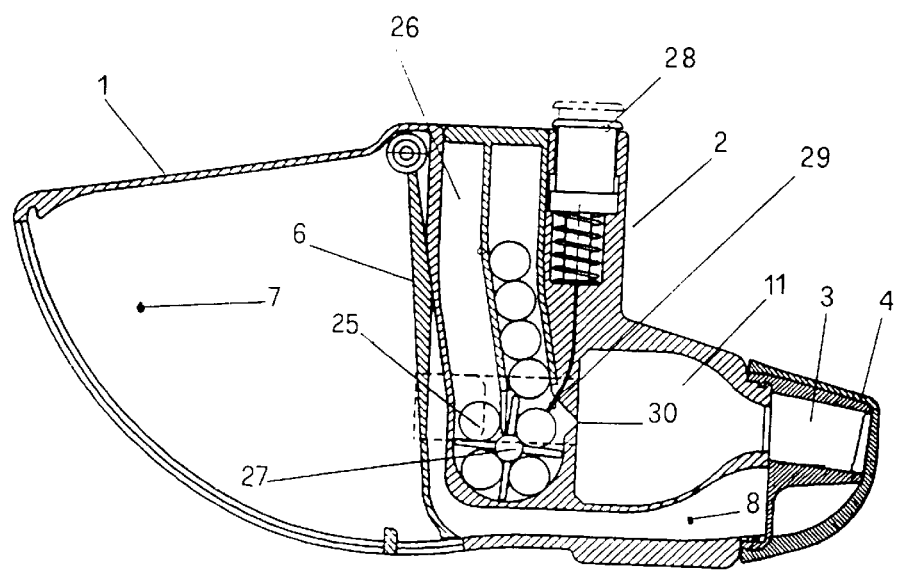
FIG. 11 is a vertical section of a further embodiment of the present invention, comprising devices suitable for delivering a drug in the form of a powder.

FIG. 11 shows a vertical section of a further embodiment of the present invention comprising delivery devices 2 suitable for delivering the drug in the form of a powder.

The drug is contained in capsules 25 inserted in a horizontal position in a loader 26 and, moved ahead by a revolving device 27 started by the patient in a known manner.

To take the drug, the patient removes the protective cap 4 uncovering the mouthpiece 3, acts on the push-button 28 (having a return spring) connected to the blade 29 which cuts the envelope of the capsule 25 connected with the nozzle 30, the nozzle being preferably but not necessarily of a different shape than the nozzle 15 of FIG. 1, provided on the back wall of the expansion chamber 11. The patient then starts to inspire, causing a vacuum in the expansion chamber 11, which draws the powder contained in the capsule 25 cut by the blade 29 through the nozzle 30 into the expansion chamber.

In the expansion chamber 11 the powder mixes with the air which enters through the side openings 5 (FIG. 1) and the patient takes the drug while he is inspiring through the mouthpiece 3, as an air-powder mixture which has formed in the expansion chamber 11.

Without going beyond the scope of the present invention, a technician can modify and improve the device for the treatment of asthmatic patients which is the subject-matter of the present invention according to experience and to the natural progress of technology.

We claim:

1. A hand held device for the treatment of asthmatic patients, comprising:
    a casing dimensioned to fit in a hand of a patient, the casing having a mouthpiece;
    a mechanical flow meter device disposed in the casing for measuring peak expiratory flow rate from the mouthpiece;
    a manually actuated drug dispenser disposed in the casing for dispensing drugs for treating asthma to the mouthpiece when manually actuated by the patient
    said device having a first and second configuration, said mouthpiece being in communication with said mechanical flow meter device in said first configuration, and said mouthpiece being in communication with said manually actuated drug dispenser in said second configuration.

2. The device according to claim 1, further comprising an expansion chamber disposed in the casing adjacent the drug dispenser between a nozzle for delivering said drug and the mouthpiece of said device, said expansion chamber receiving ambient air to be mixed with said drug through openings provided on the casing of said device.

3. The device according to claim 2, wherein the drug is delivered as a pressurized atomized liquid, said drug being contained in a pressure cylinder comprising a cylindrical base a delivery valve of said drug disposed at one end of the cylindrical base, a cylindrical body and a connecting surface for connecting said cylindrical body to said base.

4. The device according to claim 3, further comprising a seat formed as a cavity in the casing communicating with the drug dispenser, having such form and dimensions to be suitable for receiving a variety of said pressure cylinders.

5. The device according to claim 4, wherein said seat comprises:
   a first zone having a diameter not smaller than a maximum diameter of said cylindrical body of said pressure cylinders;
   a second zone, underneath said first zone, having a diameter not smaller than the diameter of said base of said pressure cylinders and a height not greater than the minimum height of said connecting surface of said pressure cylinders; and
   a flared hole provided at the bottom of said second zone and connected to said nozzle for delivering the drug by a duct, for fitting a delivery valve of the pressure cylinder disposed in the seat.

6. The device according to claim 3, further comprising a device suitable for preventing the delivery of said drug from the pressure cylinder containing said drug, said device being deactivated by a patient at the beginning of inspiration.

7. The device according to claim 6, further comprising a lever movable in a chamber provided in said device and connected to said expansion chamber by a passage, said lever being pivotable on a pivot disposed in said chamber; so that when in a locking position, an end of a first arm of said lever engages against said base of said cylinder blocking its downward motion and preventing said delivery valve of said cylinder from being started; and so that, in response to the vacuum caused in said expansion chamber by the patient inspiring, the end of a second arm of said lever moves towards said expansion chamber, rotating said lever around said pivot, and disengages the end of said first arm of said lever from the base of said cylinder, allowing drug delivery to be started.

8. The device according to claim 7, wherein said lever is kept in a locking position by elastic means.

9. The device according to claim 2, wherein said drug delivered in the treatment of asthma is in the form of a powder.

10. The device according to claim 9, for further comprising:
   a loader formed within the casing, and adapted to contain a plurality of capsules containing said drug in the form of a powder, said capsules being insertable in the loader;
   a nozzle connecting the loader to the expansion chamber;
   a revolving device disposed within the loader and activated by the patient, adapted for moving ahead the plurality of capsules containing said drug in the form of a powder; and
   a device for cutting the capsules, disposed in the casing adjacent to the loader, activatable by a patient and comprising a push-button held in a first position by a return spring and movable to a second position by a force applied by a patient, a blade suitable for rending the envelope of the capsule disposed adjacent to the nozzle when the push-button is moved to the second position; so that, in response to the vacuum caused by a patient in said expansion chamber during the inspiration performed to take the drug, said drug in the form of a powder contained in said capsule rent by said blade is drawn through said nozzle, to said expansion chamber, wherein it mixes with ambient air and is inhaled by a patient.

11. The device according to claim 1, wherein said mouthpiece is rotatably joined to the casing, to allow a patient to select which of the mechanical flow meter and the drug dispenser communicates with the mouthpiece, by rotating said mouthpiece in alignment with a duct to said mechanical flow meter, or in alignment with a duct to said drug dispenser, said mouthpiece having an inner surface defining a flow passage.

12. The device according to claim 11, wherein an annular ridge extends from the inner surface of said mouthpiece, adjacent to an end of the mouthpiece rotatably joined to the casing, said annular ridge being suitable for engaging a corresponding annular groove provided on an external surface of said casing at an end adjacent to the mouthpiece, the rotation of said ridge in said annular groove allowing a patient to select which of the mechanical flow meter and the drug dispenser communicates with the mouthpiece.

13. The device according to claim 2, wherein the expansion chamber has a generally cylindrical shape, tapering to a smaller diameter at one end and flattened on one side, and has a diameter of between 25 mm and 30 mm, has a maximum height of between 20 mm and 25 mm and has a total length of between 30 mm and 40 mm.

\* \* \* \* \*

UNITED STATES PATENT AND TRADEMARK OFFICE
CERTIFICATE OF CORRECTION

PATENT NO. : 5,769,070
DATED : June 23, 1998
INVENTOR(S) : Franco FRATI, Claudio ALBIANI It is certified that error appears in the above-identified patent and that said Letters Patent is hereby corrected as shown below:

In claim 1, col. 6, line 45, after "patient", insert --;--.
In claim 3, col. 6, line 61, after "base", insert --,--.
In claim 10, col. 7, line 39, before "further", delete "for".
In claim 13, col. 8, line 41, after "25 mm", insert --,--.

Signed and Sealed this

First Day of September, 1998

Attest:

BRUCE LEHMAN

*Attesting Officer*  *Commissioner of Patents and Trademarks*